US012675936B2

(12) United States Patent
Lagrandie et al.

(10) Patent No.: US 12,675,936 B2
(45) Date of Patent: Jul. 7, 2026

(54) METHOD FOR REGISTERING THREE-DIMENSIONAL REPRESENTATIONS OF AN OBJECT ON THE OBJECT ITSELF AND DEVICE FOR PROVIDING NAVIGATION ASSISTANCE IN AN OBJECT IMPLEMENTING SAID METHOD

(71) Applicant: COLLIN, Bagneux (FR)

(72) Inventors: Fabrice Lagrandie, Bagneux (FR);
Stéphane Mazalaigue, Bagneux (FR);
Guillaume Kazmitcheff, Bagneux (FR)

(73) Assignee: COLLIN, Bagneux (FR)

( * ) Notice: Subject to any disclaimer, the term of this patent is extended or adjusted under 35 U.S.C. 154(b) by 155 days.

(21) Appl. No.: 18/852,891

(22) PCT Filed: Mar. 24, 2023

(86) PCT No.: PCT/IB2023/052948
§ 371 (c)(1),
(2) Date: Sep. 30, 2024

(87) PCT Pub. No.: WO2023/187589
PCT Pub. Date: Oct. 5, 2023

(65) Prior Publication Data
US 2025/0218101 A1 Jul. 3, 2025

(30) Foreign Application Priority Data
Mar. 31, 2022 (FR) ...................................... 2202970

(51) Int. Cl.
*G06T 15/00* (2011.01)
*G16H 30/40* (2018.01)
(52) U.S. Cl.
CPC ............. *G06T 15/00* (2013.01); *G16H 30/40* (2018.01)

(58) Field of Classification Search
CPC ................................ G06T 15/00; G16H 30/40
See application file for complete search history.

(56) References Cited

U.S. PATENT DOCUMENTS

2005/0180623 A1* 8/2005 Mueller ............... H04N 13/254
348/E13.016

FOREIGN PATENT DOCUMENTS

DE 102004049258 A1 * 4/2006 ........... G06F 3/0325
DE 10 2004 049258 B4 4/2007
WO WO-2018006168 A1 * 1/2018 ............. A61B 34/20

OTHER PUBLICATIONS

Lee, Jiann-Der, et al. "A Coarse-to-Fine Surface Registration Algorithm for Frameless Brain Surgery." (2007). (Year: 2007).*

(Continued)

*Primary Examiner* — Daniel F Hajnik
*Assistant Examiner* — Sarah Yeo Lee
(74) *Attorney, Agent, or Firm* — CUSHMAN PARTNERS, LLC

(57) ABSTRACT

A registration method includes a storage of two three-dimensional representations of an object and locations of at least three reference points of the object in these two three-dimensional representations; an angular registration of the first three-dimensional representation on the object from a recording of locations of the reference points of the object in a reference frame linked to a reference ancillary fixed on the object; a surface registration of the first three-dimensional representation on the object, including a recording of locations of surface points other than the reference points on the surface of the object in the three-dimensional reference frame linked to the referencing ancillary; and a registration of the second three-dimensional representation of the object on the object itself including a surface registration of this second three-dimensional representation on the basis of the (Continued)

Figure 2:
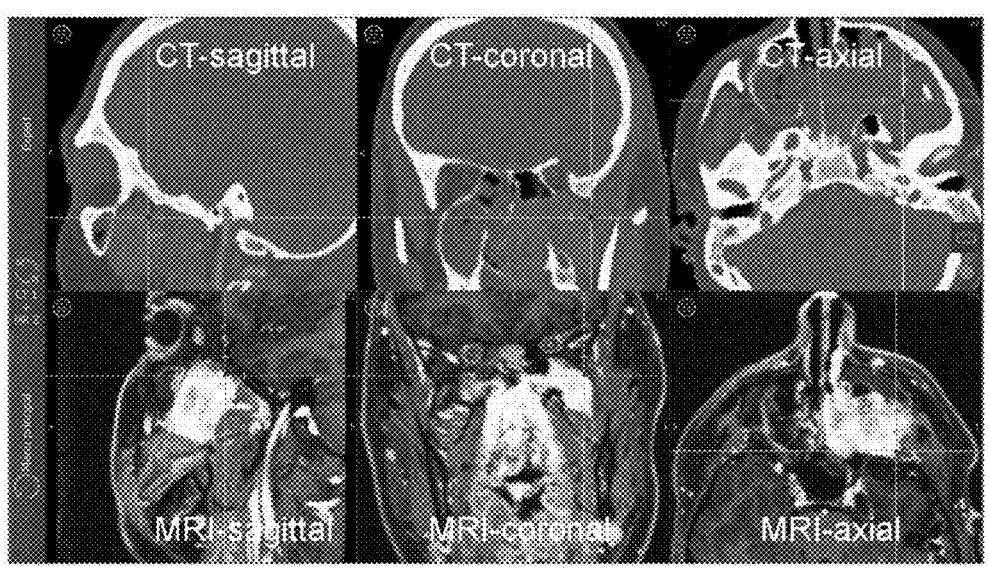

recording of the surface point locations made for the surface
registration of the first three-dimensional representation.

15 Claims, 3 Drawing Sheets

(56)                    References Cited

OTHER PUBLICATIONS

International Search Report as issued in International Patent Appli-
cation No. PCT/IB2023/052948, dated Jul. 14, 2023.
Lee, J.-D., et al., "A Coarse-to-Fine Surface Registration Algorithm
for Frameless Brain Surgery," 2007 Annual International Confer-
ence of the IEEE Engineering in Medicine and Biology Society:
[EMBC '07], [In Conjunction With the Biennial Conference of the
Societe Francaise De Genie Biologique Et Medical, Aug. 2007, pp.
836-839, XP031336299.

* cited by examiner

Figure 1

METHOD FOR REGISTERING THREE-DIMENSIONAL REPRESENTATIONS OF AN OBJECT ON THE OBJECT ITSELF AND DEVICE FOR PROVIDING NAVIGATION ASSISTANCE IN AN OBJECT IMPLEMENTING SAID METHOD

CROSS-REFERENCE TO RELATED APPLICATIONS

This application is the U.S. National Stage of PCT/IB2023/052948, filed Mar. 24, 2023, which in turn claims priority to French patent application number 2202970 filed Mar. 31, 2022. The content of these applications are incorporated herein by reference in their entireties.

The present invention relates to a method for three-dimensional registering three-dimensional representations of an object on the object itself, using a referencing ancillary fixed to the object and a stylus a tip of which can be located in a three-dimensional reference frame linked to the referencing ancillary. It also concerns a computer program comprising instructions for executing the steps of such a method, as well as a device for navigation assistance in an object implementing this registration method.

The invention applies more particularly to a method of this type comprising:

a memory storage of a first three-dimensional representation of the object according to a first three-dimensional imaging mode and of locations of at least three reference points of the object in this first three-dimensional representation;

a three-dimensional angular registration, by a computing unit, of this first three-dimensional representation on the object from a recording, using the tip of the stylus, of locations of the object's reference points in the three-dimensional reference frame linked to the referencing ancillary;

a three-dimensional surface registration, by the computing unit, of this first three-dimensional representation on the object comprising:

extracting a surface of the object in the first three-dimensional representation, recording, using the stylus tip, the locations of a plurality of surface points other than the reference points on the surface of the object in the three-dimensional reference frame linked to the referencing ancillary, and computing the three-dimensional surface registration from this surface point location recording.

Such a three-dimensional registration method is used, for example, in a device for navigation assistance in an object by means of an instrument with a functional tip, such as the surgical navigation device marketed under the registered trademark "Collin Navigation Solutions" and intended for otorhinolaryngology operations. The object is then the head of a human or animal patient inside which an intervention, using a surgical instrument, is to be envisaged via the auditory, nasal or buccal route. This is a non-limiting example of an industrial application of the present invention.

More precisely, the three-dimensional angular registration achieved by recording the locations of reference points chosen by a practitioner both in the first three-dimensional representation of the object and on the object itself facilitates, by simplifying it, the computation of a transition matrix between the reference frame linked to the object, i.e. that linked to the referencing ancillary, and a reference frame linked to the first three-dimensional representation. This simplification results from a limitation of possible solutions in the well-known algorithmic resolution of the transition matrix computation.

In addition, the following can be provided:

memory storage of a second three-dimensional representation of the object according to a second three-dimensional imaging mode, other than the first three-dimensional imaging mode, and of locations of the reference points of the object in this second three-dimensional representation; and three-dimensional registration of this second three-dimensional representation of the object on the object itself.

More generally, more than two three-dimensional representations can be recorded and registered in three dimensions. However, each three-dimensional registration, even when simplified by taking reference point locations, remains algorithmically complex and therefore costly in terms of computing time. Multiplying the number of three-dimensional representations that can be recorded, registered and displayed for a device for navigation assistance in an object is therefore certainly very interesting from the point of view of a multimodal approach to intervention in the object, but it does have certain limitations.

Another solution might be to register the first three-dimensional representation on the object, and then to register, in particular merge, each other three-dimensional representation on the first. In reality, however, this is no simpler. In addition, the registration methods using data fusion known in medical imaging, notably between scanner and magnetic resonance imaging, are not satisfactory for an application in otorhinolaryngology, which takes advantage of separate displays for the different acquisition modes.

It may thus be desirable to provide a three-dimensional registration method which avoids at least some of the above-mentioned problems and constraints.

A method is therefore proposed for three-dimensional registration of three-dimensional representations of an object on the object itself, using a referencing ancillary fixed to the object and a stylus, a tip of which can be located in a three-dimensional reference frame linked to the referencing ancillary, comprising:

a memory storage of a first three-dimensional representation of the object according to a first three-dimensional imaging mode and of locations of at least three reference points of the object in this first three-dimensional representation;

a three-dimensional angular registration, by a computing unit, of this first three-dimensional representation on the object from a recording, using the tip of the stylus, of locations of the object's reference points in the three-dimensional reference frame linked to the referencing ancillary;

a three-dimensional surface registration, by the computing unit, of this first three-dimensional representation on the object comprising:

extracting a surface of the object in the first three-dimensional representation, recording, using the stylus tip, the locations of a plurality of surface points other than the reference points on the surface of the object in the three-dimensional reference frame linked to the referencing ancillary, and computing the three-dimensional surface registration from this surface point location recording;

a memory storage of a second three-dimensional representation of the object according to a second three-dimensional imaging mode, other than the first three-dimensional imaging mode, and of locations of the reference points of the object in this second three-dimensional representation; and a three-dimensional registration of this second three-dimensional representation of the object on the object itself;

wherein the three-dimensional registration of the second three-dimensional representation comprises a three-dimensional surface registration of this second three-dimensional representation, by the computing unit, on the basis of the recording of the locations of surface points carried out for the surface registration of the first three-dimensional representation.

Taking advantage of the surface point location recording performed for the surface registration of the first three-dimensional representation, to perform the three-dimensional surface registration of the second three-dimensional representation, is a trick that simplifies the three-dimensional registration of any recordable three-dimensional representation from the second, since the same method can be applied to a third three-dimensional representation substituting for the second, and so on. This also makes it possible to increase the number of surface points to be located by stylus to improve the quality of each three-dimensional surface registration, without increasing the complexity and duration of the registration protocol.

Optionally, the three-dimensional registration of the second three-dimensional representation comprises a three-dimensional angular registration, by the computing unit, of this second three-dimensional representation on the object on the basis of the recording, carried out for the three-dimensional angular registration of the first three-dimensional representation, of the locations of the reference points of the surface of the object in the three-dimensional reference frame linked to the referencing ancillary.

Also optionally:

the three-dimensional surface registration of the first three-dimensional representation on the object involves computing a first transition matrix between the locations of the recorded surface points and their locations on the surface of the object as extracted in the first three-dimensional representation; and the three-dimensional surface registration of the second three-dimensional representation comprises extracting a surface of the object in the second three-dimensional representation and computing a second transition matrix between the locations of the surface points recorded for the surface registration of the first three-dimensional representation and their locations on the surface of the object as extracted in the second three-dimensional representation.

Also optionally, the three-dimensional surface registration of the first three-dimensional representation on the object comprises recording the locations of several hundred surface points other than the reference points on the surface of the object in the three-dimensional reference frame linked to the referencing ancillary, preferably between 200 and 1000 surface points, even more preferably between 500 and 600 surface points.

Also optionally, a three-dimensional registration method according to the invention comprises the prior acquisition of:

the first three-dimensional representation in the form of a volume image of the object by scanner or CT scan; and the second three-dimensional representation in the form of a volume image of the object by magnetic resonance.

Also optionally, the object is a human or animal patient's head and the referencing ancillary is a device fixed to this head with a stability capable of inducing a submillimeter registration error, for example a forehead band fixed stably to the patient's forehead, a forehead pin fixed stably to the patient's forehead or a buccal device clamped in the patient's mouth between their teeth.

Also optionally, the reference points of the patient's head are non-aligned, comprising for example at least one nasion localization point, one naso-labial junction localization point and one external orbital rim localization point when the referencing ancillary is stably fixed to the patient's forehead.

It is also proposed a computer program downloadable from a communication network and/or stored on a computer-readable medium and/or executable by a processor, comprising instructions for executing the steps of a method for three-dimensional registering three-dimensional representations of an object on the object itself according to the invention, when said program is executed by a computing unit of a device for navigation assistance in the object with the aid of an instrument with a functional end, and when this device further comprises:

a memory for storing a first three-dimensional representation of the object according to a first three-dimensional imaging mode, locations of at least three reference points of the object in this first three-dimensional representation, a second three-dimensional representation of the object according to a second three-dimensional imaging mode other than the first three-dimensional imaging mode, and locations of the reference points of the object in this second three-dimensional representation;

a referencing ancillary designed to be attached to the object; and a stylus that can be manipulated by an operator, a tip of which can be located in a three-dimensional reference frame linked to the referencing ancillary.

Also proposed is a device for navigation assistance in an object by means of an instrument with a functional end, comprising:

a memory for storing a first three-dimensional representation of the object according to a first three-dimensional imaging mode, locations of at least three reference points of the object in this first three-dimensional representation, a second three-dimensional representation of the object according to a second three-dimensional imaging mode other than the first three-dimensional imaging mode, and locations of the reference points of the object in this second three-dimensional representation;

a computing unit designed for three-dimensional registration of said first and second three-dimensional representations of the object on the object itself;

a referencing ancillary intended for attachment to the object;

a stylus, a tip of which can be located in a three-dimensional reference frame linked to the referencing ancillary;

wherein the computing unit is more specifically designed to execute:

a three-dimensional angular registration of the first three-dimensional representation on the object based on a recording, by interaction with the tip of the stylus when manipulated by an operator, of the locations of the object's reference points in the three-dimensional reference frame linked to the referencing ancillary;

a three-dimensional surface registration of the first three-dimensional representation on the object comprising:

an extraction of a surface of the object in the first three-dimensional representation, a recording, by interaction with the tip of the stylus when manipulated by an operator, of locations of a plurality of surface points other than the reference points on the surface of the object in the three-dimensional reference frame linked to the referencing ancillary, and the computing of the three-dimensional surface registration from this recording of surface point locations;

the computing unit being further designed so that the three-dimensional registration of the second three-dimensional representation comprises a three-dimensional surface registration of this second three-dimensional representation on the basis of the recording of the locations of the surface points carried out for the surface registration of the first three-dimensional representation.

Optionally, a device for navigation assistance in an object according to the invention may further comprise:

an instrument, a functional end of which can be located in the three-dimensional reference frame linked to the referencing ancillary; and a screen for simultaneous display of several planar cross-sectional reconstructions of the object, including at least two planar reconstructions of the same cross-section of the object obtained respectively from one and the other of the first and second three-dimensional representations;

wherein the computing unit is designed to perform:

locating and visually displaying the functional end of the instrument in each planar cross-sectional reconstruction of the object displayed on the screen; and switching the display between several planar cross-sectional reconstructions of the object according to the first three-dimensional representation, several planar cross-sectional reconstructions of the object according to the second three-dimensional representation and several planar cross-sectional reconstructions of the object according to the first and second three-dimensional representations, this switching being activatable by a predetermined approach between the functional end of the instrument and a calibration pin of the referencing ancillary.

The invention will be better understood with the aid of the following description, given solely by way of example and with reference to the appended drawings wherein:

Figure 1:
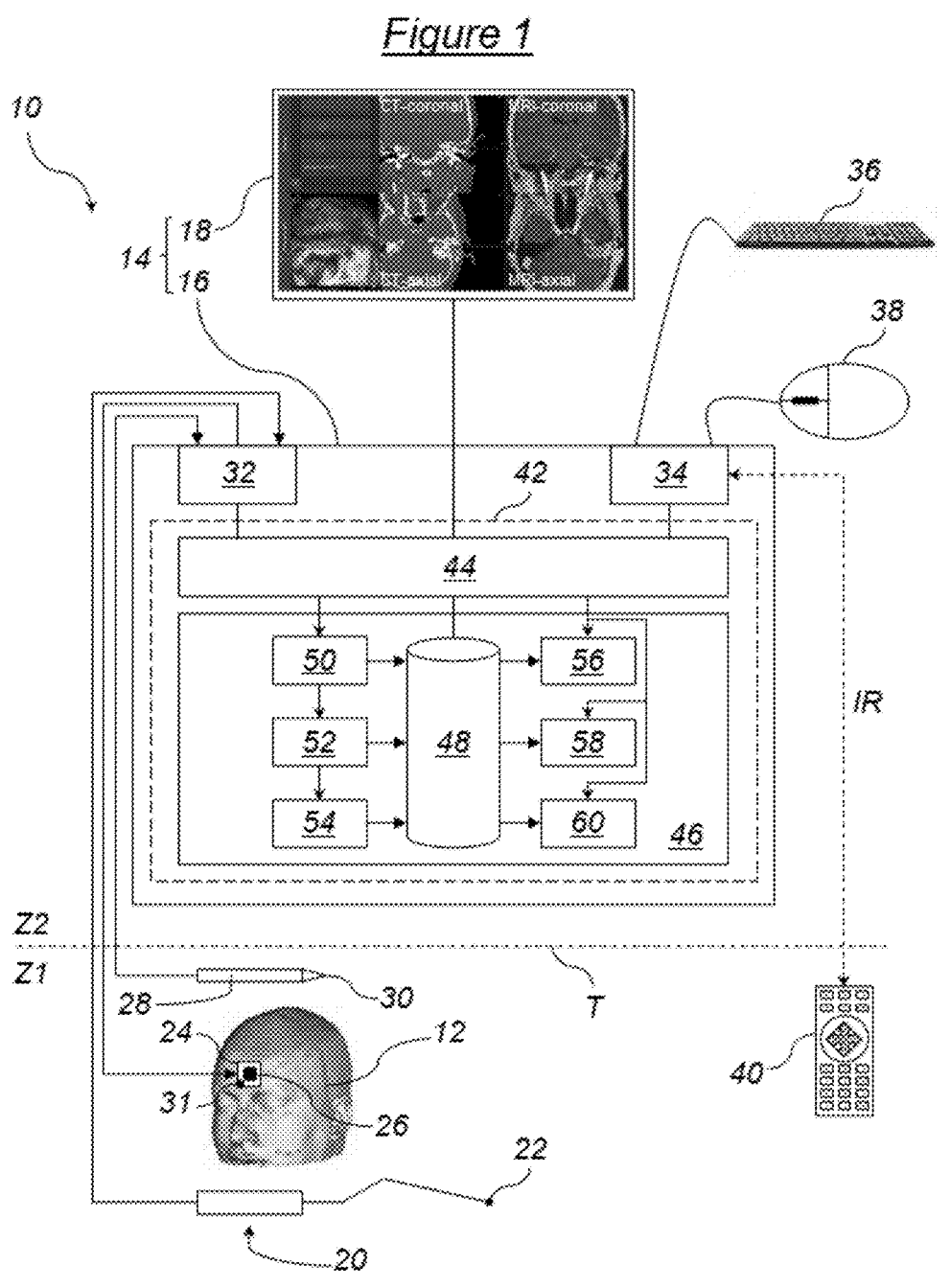

FIG. 1 diagrammatically represents the general structure of a device for navigation assistance in an object, according to an embodiment of the invention, FIG. 2 illustrates an example of the simultaneous display of several planar cross-sectional reconstructions of the object shown in FIG. 1, obtained from two different three-dimensional representations, as can be obtained on a screen of the navigation assistance device shown in FIG. 1.

Figure 3:
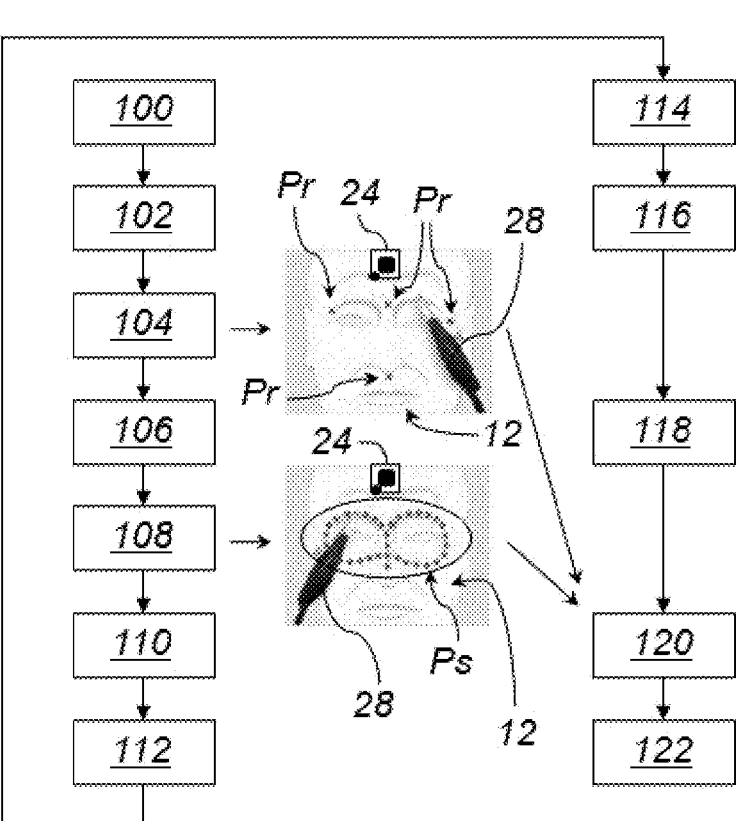

FIG. 3 illustrates the successive steps of a method for the three-dimensional registration of three-dimensional representations of the object shown in FIG. 1 on itself, as can be implemented by the navigation assistance device shown in FIG. 1.

The device 10 for navigation assistance in an object 12 shown diagrammatically in FIG. 1 comprises a movable navigation unit 14 comprising a main housing 16 with electrical, electronic and software components, for example mounted on castors and fitted with a handle (not shown) to be moved by a practitioner, and a display screen 18, for example a touch screen, integral with the main housing 16. In the non-limiting example shown in FIG. 1, this is more precisely a surgical navigation device intended for otorhinolaryngology (ENT) operations. In this case, object 12 is the head of a human or animal patient, inside which an operation is to be performed via the auditory, nasal or buccal route.

To this end, the navigation assistance device 10 further comprises an instrument 20 with a functional end 22, such as an ENT surgical instrument with suction cannula, rotating tip, pliers or any other functional end 22 useful for an ENT surgical operation via the auditory, nasal or buccal route.

For the implementation of a method for three-dimensional registration of three-dimensional representations of the object 12 on the object 12 itself, as well as a method of navigation assisted by tracking, on the display screen 18, a displacement of the functional end 22 of the surgical instrument 20 in internal cavities of the patient's head 12, the navigation assistance device 10 further comprises:

a referencing ancillary device 24 with an active electromagnetic locating element 26 (i.e. an electromagnetic sensor with a transmitting function), intended to be fixed in a manner known per se to the patient's head 12, and a registration stylus 28, a distal tip 30 of which can be located in a three-dimensional reference frame linked to the registration ancillary device 24, this reference frame also being linked to the patient's head 12 when the registration ancillary device 24 is attached to it.

The methods for attaching the referencing ancillary 24 to the head 12 are known per se and will not be described in detail. For example, they are advantageously defined in such a way as to ensure that the fixation is stable enough to induce a registration error, and therefore a navigation tracking error, that is sub-millimeter.

FIG. 1 illustrates a referencing ancillary 24 in the form of a forehead pin stably fixed to the patient's forehead by double-sided adhesive tape, but any other well-known referencing ancillary is also suitable: for example, a forehead band stably fixed to the patient's forehead, a buccal device clamped in the patient's mouth between their teeth, a bone device screwed laterally into the patient's skull, or any other form of referencing ancillary suitable for ENT surgery.

It should be noted that the way in which the distal tip 30 of the registration stylus 28 can be located in the three-dimensional reference frame linked to the referencing ancillary 24 (using an electromagnetic sensor with a reception function, for example) is well known, so the electromagnetic technology implemented for such location will not be detailed. The same technology is also used to locate the surgical instrument 20 in the three-dimensional reference frame linked to the referencing ancillary 24 (also using an electromagnetic sensor with a reception function, for example). More precisely, to ensure that its potentially interchangeable functional end 22 is itself directly locatable in the three-dimensional reference frame linked to the referencing ancillary 24, the surgical instrument 20 may need to be calibrated. This calibration, carried out with the aid of a calibration pin 31 attached to the referencing ancillary 24, or with the aid of the registration stylus 28, is also well known, so it will not be detailed here either.

It should also be noted that, during a procedure involving the aforementioned three-dimensional registration of three-dimensional representations of object 12 on object 12 itself, calibration of surgical instrument 20 or assisted navigation, the patient's head 12, to which the referencing ancillary 24 is attached, the registration stylus 28 and the surgical instrument 20 must be isolated from any disturbance, in particular any disturbance due to excessive proximity to the movable navigation unit 14. For this reason, the operating field Z1 wherein the patient's head 12, the referencing ancillary 24, the registration stylus 28 and the surgical instrument 20 are located is remote and well isolated from the navigation assistance field Z2 wherein the movable navigation unit 14 is located. This distance, or isolation, is marked in FIG. 1 by the horizontal dashed line T.

To interact with the referencing ancillary 24, the registration stylus 28 and the surgical instrument 20, the main housing 16 is equipped with an electromagnetic field-generating spatial localization interface 32. This is an electronic element for determining the three-dimensional spatial coordinates of a specific sensor, such as those embedded in the referencing ancillary 24, the registration stylus 28 and the surgical instrument 20. Such a spatial localization interface 32 is well known, so it will not be detailed here.

The main housing 16 is also provided with an interface 34 for connection to other possible peripherals, such as a keyboard 36, a mouse 38 and/or a remote control 40. The remote control 40, for example, is connected via a wireless IR link of infrared type, enabling it to be used in the operating field Z1. Interface 34 may also include a USB port, a CD-ROM drive, or any other video input for recording a three-dimensional representation of object 12 previously acquired in any three-dimensional imaging mode.

The main housing 16 also comprises several functional modules which will be described below. In the example described, these modules are software. Thus, the main housing 16 comprises a computer-like element 42 including a processing unit 44, interacting with the spatial localization interface 32, the interface 34 and the display screen 18, and an associated memory area 46 wherein a data storage area 48 and several computer programs 50 to 60 or several functions of the same computer program are stored. These computer programs comprise instructions designed to be executed by the processing unit 44 in order to realize the functions of the software modules. They are presented as distinct, but this distinction is purely functional. They could just as easily be grouped together in any combination to form one or more software modules. Their functions could also be at least partly micro-programmed or micro-wired into dedicated integrated circuits, such as digital circuits. Alternatively, the computer 42 could thus be replaced by an electronic device consisting solely of digital circuits (without computer programs) to perform the same functions.

The main housing 16 thus firstly comprises a software module 50, to be executed by the processing unit 44, for recording in memory 46, more precisely in data storage area 48, three-dimensional representations of the object 12, otherwise generally referred to as "series", according to any three-dimensional imaging modes, preferably according to one or more imaging modes by scanner (i.e. by CT scan) or MRI (i.e. for "Magnetic Resonance Imaging") with or without injection of contrast medium(s). In general, any three-dimensional imaging method that makes it possible to extract a surface from object 12 is suitable, bearing in mind that scanner series are mainly used in ENT surgery. A limit can be set in terms of the number of series that can be recorded in data storage area 48, for example four.

The main housing 16 further includes a software module 52, to be executed by the processing unit 44, for three-dimensional angular registration of each three-dimensional representation of the object 12 stored in the data storage area 48 on the object 12 itself.

According to an example of an angular registration protocol, which is advantageously implemented but not limitative, particularly if a first three-dimensional representation is to be angularly registered, at least three predetermined reference points of the object 12 are located in the three-dimensional representation concerned and recorded in data storage area 48, then these same reference points are located in the three-dimensional reference frame linked to the referencing ancillary 24 using the tip 30 of the stylus 28 in a manner known per se, and they are recorded in data storage area 48 too. If a second or subsequent three-dimensional representation is to be angularly registered, while the first three-dimensional representation has already been angularly registered, it may be sufficient to locate the reference points of object 12 in the relevant three-dimensional representation and save them in data storage area 48 without having to locate these same reference points again in the three-dimensional reference frame linked to the referencing ancillary 24 using stylus 28, since the angular registration can take advantage of the locations recorded with the stylus 28 for the first three-dimensional representation, as they have a priori no reason to be different.

It is advisable to choose reference points which are as little aligned as possible to make angular registration effective and precise. For example, when the referencing ancillary 24 is a headband or pin stably fixed to the patient's forehead, the reference points generally chosen are a nasion localization point, a naso-labial junction localization point and a left and/or right external orbital rim localization point. By convention, they indicate main north, south, west and/or east orientations. Any other reference point may be freely chosen, depending on where the referencing ancillary 24 is attached, the intended application and, more generally, the nature of the object 12.

The main housing 16 further includes a software module 54, to be executed by the processing unit 44, for three-dimensional surface registration of each three-dimensional representation of the object 12 stored in the data storage area 48 on the object 12 itself.

According to an example of a surface registration protocol which is advantageously implemented but which is not limitative, if a first three-dimensional representation is to be registered, a surface of the object 12 in the three-dimensional representation concerned is first extracted and recorded in data storage area 48. This can usually be done automatically, provided that good conditions for acquiring this three-dimensional representation have been met. It also involves locating a plurality of surface points other than the reference points on the surface of the object 12 in the three-dimensional reference frame linked to the referencing ancillary 24, using the tip 30 of the stylus 28, and recording them in the data storage area 48. Finally, it involves computing the three-dimensional surface registration from this recording of surface point locations.

More precisely, three-dimensional surface registration of the first three-dimensional representation on the object 12 involves computing a first transition matrix between the previously recorded surface point locations and their locations on the surface of the object 12 as extracted in the first three-dimensional representation. Prior angular registration facilitates the computation of this first transition matrix by limiting the possible solutions.

If a second or subsequent three-dimensional representation is to be registered, while the first three-dimensional representation has already been registered according to the above-mentioned surface registration protocol, it may be sufficient to extract a surface from the object 12 in the three-dimensional representation concerned and record it in data storage area 48, then directly carry out a three-dimensional surface registration of this second or subsequent three-dimensional representation, based on the recording of surface point locations carried out for the surface registration of the first three-dimensional representation. This approach is highly advantageous, as the recording of surface point locations can be tedious and time-consuming.

More precisely, the three-dimensional surface registration of the second or subsequent three-dimensional representation on the object 12 involves computing a second transition matrix between the surface point locations previously recorded for the surface registration of the first three-dimensional representation and their locations on the surface of the object 12 as extracted in the second or subsequent three-dimensional representation. Similarly, the prior angular registration of the second or subsequent three-dimensional representation facilitates the computation of this second passage matrix by limiting the possible solutions.

In practical terms, a large number of surface points can be located by moving the tip 30 of the stylus 28 over the patient's head 12, particularly around reference points. There is no real limit. For example, several hundred surface points are advantageously located in the three-dimensional reference frame linked to the referencing ancillary 24 for the most accurate surface registration possible in ENT surgery, preferably between 200 and 1000 surface points, even more preferably between 500 and 600 surface points.

The main housing 16 further includes a software module 56, to be executed by the processing unit 44, for selecting a display to assist navigation using the surgical instrument 20 when each three-dimensional representation stored in data storage area 48 has been registered by executing software modules 52 and 54. In particular, when two registered three-dimensional representations are available in memory 46, for example one in the form of a volumetric image of object 12 by scanner, the other in the form of a volumetric image of object 12 by magnetic resonance, the software module 56 manages the possible selection of a simultaneous display of several planar cross-sectional reconstructions of the object 12, including at least two planar reconstructions of the same cross-section of the object 12 obtained respectively from one and the other of the first and second three-dimensional representations.

In ENT surgery, planar cross-sectional reconstructions of object 12 generally include sagittal, axial and coronal sections. They are obtained by a computation known per se, in particular by interpolation, from real sections acquired according to the imaging mode in question. In the example shown on the display screen 18 of FIG. 1, an upper left window illustrates a menu enabling you to select one of several predetermined display modes, to calibrate the surgical instrument 20 or to review the registration and reference points of the available three-dimensional representations. A lower left window shows real-time video tracking of the surgical instrument 20 in operating mode, using an endoscopic camera. An upper central window illustrates a coronal planar reconstruction by scanner, including positioning of the functional end 22 of the surgical instrument 20. An upper right window shows the same coronal planar reconstruction by MRI, including positioning of the functional end 22 of the surgical instrument 20. A lower central window illustrates a CT axial planar reconstruction including a positioning of the functional end 22 of the surgical instrument 20. A lower right window illustrates the same axial planar reconstruction by MRI, including positioning of the functional end 22 of the surgical instrument 20. This makes it possible to appreciate the position of the functional end 22 of the surgical instrument 20 on both CT and MRI imaging modes at the same time.

The main housing 16 further includes a software module 58, to be executed by the processing unit 44, for real-time tracking of the functional end 22 of the surgical instrument 20 and for updating at any time each of the planar reconstructions displayed simultaneously on the screen 18 which include it.

The main housing 16 further includes a software module 60, to be executed by the processing unit 44, for switching the display on the screen 18 between several planar cross-sectional reconstructions of the object 12 according to the first three-dimensional scanner representation, several planar cross-sectional reconstructions of the object 12 according to the second three-dimensional MRI representation and several planar cross-sectional reconstructions of the object 12 according to the first and second three-dimensional scanner and MRI representations, this switching being activatable in particular by a predetermined approach between the functional end 22 of the surgical instrument 20 and a specific receiver of the referencing ancillary 24, for example its calibration pin 31. This predetermined approach assumes prior calibration of the surgical instrument 20 as previously mentioned, to make its functional end 22 locatable in relation to the calibration pin 31. Advantageously, the predetermined approach is defined in terms of maximum distance and minimum duration. In other words, the predetermined approach is a distance less than or equal to Dmax between the functional end 22 of the surgical instrument 20 and the calibration pin 31 for at least a period of time Tmin. In concrete terms, Dmax is, for example, equal to 5 mm and Tmin equal to 2 s. These are the values which, experimentally, seem to work best to avoid an untimely change of display by unintentionally bringing the functional end 22 closer to the calibration pin 31 during handling. Also in practice, Dmax and Tmin can be set, for example within predefined ranges such as [2 mm; 8 mm] for Dmax and [1 s; 5 s] for Tmin. Of course, the predetermined approach designed to activate the display switching requires a particular gesture, that of positioning the functional end 22 of the surgical instrument 20 within Dmax of the calibration pin 31 for at least Tmin, but this gesture, once known, is simple and intuitive to perform.

This switching can also be activated by direct interaction with the display screen 18 when it is touch-sensitive. But this interaction is less simple and intuitive than the particular gesture mentioned above.

Each window displayed on screen 18 and showing a planar sagittal, axial or coronal cross-sectional reconstruction of object 12 can also be switched individually, for example by tactile or other interaction, to change section and/or imaging mode.

The software modules 56, 58 and 60 can be executed independently by the processing unit 44, not necessarily in the order in which they are presented above. They can also be executed at the same time.

FIG. 2 illustrates another non-limiting example of simultaneous display of several planar cross-sectional reconstructions of object 12 according to the aforementioned first and second three-dimensional scanner and MRI representations. Here, the display is subdivided into six windows. The three upper windows are respectively planar reconstructions in sagittal, coronal and axial cross-sections in scanner mode, while the three lower windows are respectively the same planar reconstructions in sagittal, coronal and axial cross-sections in MRI mode. In each window, the functional end 22 of the surgical instrument 20 is precisely located at the intersection of two axes, one horizontal and the other vertical. Visualizing and tracking the functional end 22 simultaneously in the three sagittal, coronal and axial cross-sections and in both scanner and MRI imaging modes is a valuable aid for the practitioner.

The method for three-dimensional registration of three-dimensional representations of object 12 on object 12 itself, as can be implemented by the device for navigation assistance of FIG. 1, corresponding to the execution of software modules 50, 52 and 54, will now be detailed in accordance with the successive steps of FIG. 3.

In a step 100, carried out by running software module 50, a first three-dimensional representation of object 12 according to a first three-dimensional imaging mode, for example a scanner acquisition mode, is stored in data storage area 48.

In a subsequent step 102, carried out by running software module 52, at least three predetermined reference points Pr of object 12 are located in the first three-dimensional representation and recorded in data storage area 48. In the example shown in FIG. 3, four reference points Pr are predetermined and localized: a nasion localization point, a naso-labial junction localization point, a left external orbital rim localization point and a right external orbital rim localization point.

In a subsequent step 104, carried out by running software module 52, these same reference points Pr are located in the three-dimensional reference frame linked to the referencing ancillary 24 using the tip 30 of stylus 28 in a manner known per se, and they are also recorded in data storage area 48.

In a subsequent step 106, carried out by running software module 54, a surface of object 12 is extracted from the first three-dimensional representation and recorded in data storage area 48.

In a subsequent step 108, carried out by running software module 54, a number of surface points Ps other than the reference points Pr are located on the surface of object 12 in the three-dimensional reference frame linked to the referencing ancillary 24 using the tip 30 of stylus 28, and are recorded in data storage area 48.

In a subsequent step 110, carried out by running software module 54, the three-dimensional surface registration of the first three-dimensional representation is computed from this recording of Ps surface point locations. The computation of the first transition matrix involved is facilitated by the prior angular registration achieved by performing steps 102 and 104.

In a subsequent step 112, the registration obtained from the first three-dimensional representation of the object 12 on the object 12 itself can be validated using the stylus 28 according to a protocol known per se, so that this step will not be detailed.

In a subsequent step 114, carried out by running software module 50, a second three-dimensional representation of object 12 according to a second three-dimensional imaging mode, for example according to an MRI acquisition mode, is stored in data storage area 48.

In a subsequent step 116, carried out by software module 52, the predetermined reference points Pr of object 12 are located in the second three-dimensional representation and recorded in data storage area 48.

In a subsequent step 118, carried out by running software module 54, a surface of object 12 is extracted in the second three-dimensional representation and recorded in data storage area 48.

In a subsequent step 120, carried out by running software module 54, the three-dimensional surface registration of the second three-dimensional representation is commuted from the recording of surface point Ps locations carried out in step 108. The computation of the second transition matrix involved is facilitated by the prior angular registration carried out in steps 116 and 104.

Finally, in a subsequent step 122, the registration obtained from the second three-dimensional representation of object 12 on object 12 itself can also be validated using stylus 28 according to a protocol identical to that of step 112.

It clearly appears that a method for three-dimensional registration of three-dimensional representations of an object on the object itself, such as that described above, makes it possible to envisage simultaneous display of several different three-dimensional representations of this object, facilitating and accelerating registration. This simultaneous display of several planar reconstructions in cross-section of the object using different acquisition modes, advantageously scanner and MRI but not exclusively, is a powerful tool for navigation assistance within the object for application in ENT surgery.

It should also be noted that the invention is not limited to the embodiment described above. Indeed, it will be apparent to the person skilled in the art that various modifications can be made to the embodiment described above, in the light of the teaching just disclosed to them. In the detailed presentation of the invention given above, the terms used are not to be interpreted as limiting the invention to the embodiment set out in the present description, but are to be interpreted as including all equivalents the anticipation of which is within the grasp of the person skilled in the art by applying their general knowledge to the implementation of the teaching just disclosed to them.

The invention claimed is:

1. A method for three-dimensional registering three-dimensional representations of an object on the object itself, using a referencing ancillary fixed to the object, a stylus, a tip of which can be located in a three-dimensional reference frame linked to the referencing ancillary, and an instrument, a functional tip of which can be located in the three-dimensional reference frame linked to the referencing ancillary, comprising:

a memory storage of a first three-dimensional representation of the object according to a first three-dimensional imaging mode and of locations of at least three reference points of the object in this said first three-dimensional representation;

a three-dimensional angular registration, by a computing unit, of this said first three-dimensional representation on the object from a recording, using the tip of the stylus, of locations of the object's reference points in the three-dimensional reference frame linked to the referencing ancillary;

a three-dimensional surface registration, by the computing unit, of this said first three-dimensional representation on the object comprising:

extracting a surface of the object in the first three-dimensional representation, recording the locations of a plurality of surface points other than the reference points on the surface of the object in the three-dimensional reference frame linked to the referencing ancillary, and computing the three-dimensional surface registration from said surface point location recording;

a memory storage of a second three-dimensional representation of the object according to a second three-dimensional imaging mode, other than the first three-dimensional imaging mode, and of locations of the reference points of the object in said second three-dimensional representation;

a three-dimensional registration of this said second three-dimensional representation of the object on the object itself; and a simultaneous display of several planar cross-sectional reconstructions of the object;

the three-dimensional registration of the second three-dimensional representation comprising a three-dimensional surface registration of this said second three-dimensional representation, by the computing unit, on the basis of the recording of the locations of surface points carried out for the surface registration of the first three-dimensional representation;

wherein the locations of the plurality of surface points other than the reference points on the surface of the object are recorded in the three-dimensional reference frame linked to the referencing ancillary using the tip of the stylus; and wherein the display can be switched between a plurality of planar cross-sectional reconstructions of the object according to the first three-dimensional representation, a plurality of planar cross-sectional reconstructions of the object according to the second three-dimensional representation and a plurality of planar cross-sectional reconstructions of the object according to the first and second three-dimensional representations, said switching being activatable by a predetermined approach between the functional end of the instrument and a calibration pin of the referencing ancillary.

2. The method for three-dimensional registering according to claim 1, wherein the three-dimensional registration of the second three-dimensional representation comprises a three-dimensional angular registration, by the computing unit, of said second three-dimensional representation on the object from the recording, made for the three-dimensional angular registration of the first three-dimensional representation, of the locations of the reference points of the surface of the object in the three-dimensional reference frame linked to the referencing ancillary.

3. The method for three-dimensional registering according to claim 1, wherein:

the three-dimensional surface registration of the first three-dimensional representation on the object involves computing a first transition matrix between the locations of the recorded surface points and their locations on the surface of the object as extracted in the first three-dimensional representation; and the three-dimensional surface registration of the second three-dimensional representation comprises an extraction of a surface of the object in the second three-dimensional representation and computing a second transition matrix between the locations of the surface points recorded for the surface registration of the first three-dimensional representation and their locations on the surface of the object as extracted in the second three-dimensional representation.

4. The method for three-dimensional registering according to claim 1, wherein the three-dimensional surface registration of the first three-dimensional representation on the object comprises recording the locations of several hundred surface points other than the reference points on the surface of the object in the three-dimensional reference frame linked to the referencing ancillary.

5. The method for three-dimensional registering according to claim 4, wherein the several hundred surface points comprise between 200 and 1000 surface points.

6. The method for three-dimensional registering according to claim 5, wherein the several hundred surface points comprise between 500 and 600 surface points.

7. The method for three-dimensional registering according to claim 1, comprising a prior acquisition:

of the first three-dimensional representation in the form of a volume image of the object by scanner or CT scan; and of the second three-dimensional representation in the form of a volume image of the object by magnetic resonance.

8. The method for three-dimensional registering according to claim 1, wherein the object is a human or animal patient's head and the referencing ancillary is a device fixed to said head with a stability capable of inducing a submillimeter registration error.

9. The method for three-dimensional registering according to claim 8, wherein the reference points of the patient's head are non-aligned, comprising at least one nasion localization point, one naso-labial junction localization point and one external orbital rim localization point when the referencing ancillary is stably fixed to the patient's forehead.

10. The method for three-dimensional registering according to claim 8, wherein the device is a forehead band fixed stably to the patient's forehead.

11. The method for three-dimensional registering according to claim 8, wherein the device is a forehead pin fixed stably to the patient's forehead.

12. The method for three-dimensional registering according to claim 8, wherein the device is a buccal device clamped in the patient's mouth between their teeth.

13. A non-transitory computer-readable medium, comprising instructions for executing the steps of a method for three-dimensional registering three-dimensional representations of an object on the object itself according to claim 1, when said instructions are executed by a computing unit of a device for navigation assistance in the object, and when said device further comprises:

a memory for storing a first three-dimensional representation of the object according to a first three-dimensional imaging mode, locations of at least three reference points of the object in said first three-dimensional representation, a second three-dimensional representation of the object according to a second three-dimensional imaging mode other than the first three-dimensional imaging mode, and locations of the reference points of the object in said second three-dimensional representation;

a referencing ancillary designed to be attached to the object;

a stylus, manipulable by an operator, a tip of which can be located in a three-dimensional reference frame linked to the referencing ancillary;

an instrument, a functional end of which can be located in the three-dimensional reference frame linked to the referencing ancillary; and a screen for simultaneous display of several planar cross-sectional reconstructions of the object, including at least two planar reconstructions of the same cross-section of the object obtained respectively from one and the other of the first and second three-dimensional representations.

14. A device for navigation assistance in an object, comprising:

a memory for storing a first three-dimensional representation of the object according to a first three-dimensional imaging mode, locations of at least three reference points of the object in said first three-dimensional representation, a second three-dimensional representation of the object according to a second three-dimensional imaging mode other than the first three-dimensional imaging mode, and locations of the reference points of the object in said second three-dimensional representation;

a computing unit designed for three-dimensional registration of said first and second three-dimensional representations of the object on the object itself;

a referencing ancillary for attachment to the object;

a stylus, a tip of which can be located in a three-dimensional reference frame linked to the referencing ancillary;

an instrument, a functional end of which can be located in the three-dimensional reference frame linked to the referencing ancillary; and a screen for simultaneous display of several planar cross-sectional reconstructions of the object, including at least two planar reconstructions of the same cross-section of the object obtained respectively from one and the other of the first and second three-dimensional representations;

wherein the computing unit is more precisely designed to perform:

a three-dimensional angular registration of the first three-dimensional representation on the object based on a recording, by interaction with the tip of the stylus when manipulated by an operator, of the locations of the object's reference points in the three-dimensional reference frame linked to the referencing ancillary;

a three-dimensional surface registration of the first three-dimensional representation on the object, comprising:

extracting a surface of the object in the first three-dimensional representation, recording the locations of a plurality of surface points other than the reference points on the surface of the object in the three-dimensional reference frame linked to the referencing ancillary, and computing the three-dimensional surface registration from this said surface point location recording;

the computing unit being designed so that the three-dimensional registration of the second three-dimensional representation comprises a three-dimensional surface registration of said second three-dimensional representation on the basis of the registration of locations of surface points carried out for the surface registration of the first three-dimensional representation;

wherein the recording of the locations of the plurality of surface points other than the reference points on the surface of the object in the three-dimensional reference frame linked to the referencing ancillary takes place by interaction using the tip of the stylus when it is manipulated by an operator; and wherein the computing unit is designed to switch the display between a plurality of planar cross-sectional reconstructions of the object according to the first three-dimensional representation, a plurality of planar cross-sectional reconstructions of the object according to the second three-dimensional representation and a plurality of planar cross-sectional reconstructions of the object according to the first and second three-dimensional representations, said switching being activated by a predetermined approach between the functional end of the instrument and a calibration pin of the referencing ancillary.

15. The device for navigation assistance in an object according to claim 14, wherein the computing unit is further designed to locate and visually display the functional end of the instrument in each planar cross-sectional reconstruction of the object displayed by the screen.

* * * * *